United States Patent
Ballerstadt et al.

(10) Patent No.: US 7,166,458 B2
(45) Date of Patent: Jan. 23, 2007

(54) ASSAY AND METHOD FOR ANALYTE SENSING BY DETECTING EFFICIENCY OF RADIATION CONVERSION

(75) Inventors: Ralph Ballerstadt, Houston, TX (US); Roger McNichols, Pearland, TX (US); Ashok Gowda, Houston, TX (US)

(73) Assignee: Bio Tex, Inc., Houston, TX (US)

( * ) Notice: Subject to any disclaimer, the term of this patent is extended or adjusted under 35 U.S.C. 154(b) by 0 days.

(21) Appl. No.: 10/735,153

(22) Filed: Dec. 12, 2003

(65) Prior Publication Data

US 2004/0132169 A1    Jul. 8, 2004

Related U.S. Application Data

(60) Provisional application No. 60/438,490, filed on Jan. 7, 2003.

(51) Int. Cl.
C12M 1/34 (2006.01)
C12M 3/00 (2006.01)

(52) U.S. Cl. .................... 435/287.1; 435/288.7; 435/283.1; 435/7.1; 436/529; 436/518; 436/164; 436/528; 436/172; 422/82.05; 422/50; 422/55; 422/68.1; 422/82.08

(58) Field of Classification Search .............. 435/4, 435/6, 7.1, 174, 180, 283.1, 287.1, 287.7, 435/288.7; 422/50, 52, 61, 68.1, 82.05, 55, 422/82.08; 436/501, 518, 529, 530, 528, 436/164, 172
See application file for complete search history.

(56) References Cited

U.S. PATENT DOCUMENTS

| | | | |
|---|---|---|---|
| 4,041,932 A | 8/1977 | Fostick | |
| 4,071,020 A | 1/1978 | Pugliese | |
| 4,261,968 A | 4/1981 | Ullman et al. | |
| 4,330,299 A | 5/1982 | Cerami | |
| 4,344,438 A | * | 8/1982 | Schultz ............ 600/341 |

(Continued)

OTHER PUBLICATIONS

Ballerstadt et al. A Fluorescence Affinity Hollow Fiber Sensor for Continuous Transdermal Glucose Monitoring. 2000. Analytical Chemistry. vol. 72, No. 17, pp. 4182-4192.*

(Continued)

*Primary Examiner*—Long V. Le
*Assistant Examiner*—Melanie J. Yu
(74) *Attorney, Agent, or Firm*—Neil A. Steinberg (57) ABSTRACT

In one aspect, the present invention is a system, a device and a method for sensing the concentration of an analyte in a fluid or matrix. The analyte may be glucose or any other chemical of interest. The fluid or matrix may be, for example, the fluid in a bioreactor, a food or agricultural product, any fluid or matrix in the body of an animal, or any other fluid or matrix whose concentration of an analyte is under investigation. In one embodiment, the analyte sensing device includes a housing having an interior space. Contained within the housing and in the interior space is one or more analyte sensing component(s). The analyte sensing component, in one embodiment, includes one or more radiation converting element(s), for example, converting chromophores. The radiation converting element(s) are capable of converting or modifying radiation of one or more wavelengths into radiation of one or more different wavelengths. The conversion efficiency of the radiation converting element(s) is at least partially dependent on the local concentration of an analyte within the analyte sensing component.

63 Claims, 8 Drawing Sheets

U.S. PATENT DOCUMENTS

| | | | |
|---|---|---|---|
| 4,401,122 | A | 8/1983 | Clark, Jr. |
| 4,450,104 | A * | 5/1984 | Jordan ........................ 530/396 |
| 4,868,103 | A | 9/1989 | Stavrianopoulos et al. |
| 4,954,435 | A * | 9/1990 | Krauth ...................... 435/7.93 |
| 4,981,779 | A | 1/1991 | Wagner |
| 5,001,051 | A | 3/1991 | Miller et al. |
| 5,028,787 | A | 7/1991 | Rosenthal et al. |
| 5,101,814 | A | 4/1992 | Palti |
| 5,143,066 | A | 9/1992 | Komives et al. |
| 5,244,636 | A | 9/1993 | Walt et al. |
| 5,320,814 | A | 6/1994 | Walt et al. |
| 5,326,531 | A | 7/1994 | Hahn et al. |
| 5,341,805 | A | 8/1994 | Stavridi et al. |
| 5,342,789 | A | 8/1994 | Chick et al. |
| 5,460,971 | A | 10/1995 | Gottlieb |
| 5,654,419 | A * | 8/1997 | Mathies et al. ............ 536/25.4 |
| 5,780,247 | A * | 7/1998 | Satomura et al. .......... 435/7.23 |
| 5,814,449 | A * | 9/1998 | Schultz et al. ................. 435/6 |
| 6,040,194 | A | 3/2000 | Chick et al. |
| 6,210,326 | B1 | 4/2001 | Ehwald |
| 6,256,522 | B1 * | 7/2001 | Schultz ...................... 600/317 |
| 6,267,002 | B1 | 7/2001 | Ehwald et al. |
| 6,383,767 | B1 | 5/2002 | Polak |
| 6,456,734 | B1 * | 9/2002 | Youvan et al. .............. 382/128 |
| 6,477,891 | B1 | 11/2002 | Ehwald et al. |
| 6,485,703 | B1 | 11/2002 | Cote et al. |
| 6,544,732 | B1 * | 4/2003 | Chee et al. ..................... 435/6 |
| 6,694,158 | B1 | 2/2004 | Polak |
| 6,846,638 | B1 * | 1/2005 | Shipwash ................... 435/7.1 |
| 6,942,968 | B1 * | 9/2005 | Dickinson et al. ............. 435/6 |
| 2001/0035047 | A1 | 11/2001 | Ehwald et al. |
| 2001/0045122 | A1 | 11/2001 | Ehwald et al. |
| 2002/0087145 | A1 | 7/2002 | Ehwald et al. |
| 2002/0182658 | A1 * | 12/2002 | Polak et al. ................ 435/7.92 |
| 2002/0197611 | A1 * | 12/2002 | Chagovetz ..................... 435/6 |
| 2002/0197724 | A1 * | 12/2002 | Noronha et al. .............. 436/95 |
| 2003/0027126 | A1 * | 2/2003 | Walt et al. ...................... 435/4 |
| 2003/0049625 | A1 * | 3/2003 | Heyduk ......................... 435/6 |
| 2003/0054560 | A1 | 3/2003 | Ehwald et al. |
| 2003/0059811 | A1 * | 3/2003 | Djaballah et al. .............. 435/6 |
| 2003/0147862 | A1 * | 8/2003 | Buschmann et al. ..... 424/93.21 |
| 2003/0228682 | A1 * | 12/2003 | Lakowicz et al. ......... 435/287.2 |
| 2003/0228703 | A1 * | 12/2003 | Hoppe et al. ................ 436/172 |
| 2004/0209282 | A1 * | 10/2004 | Ault-Riche et al. ............. 435/6 |

OTHER PUBLICATIONS

"Fiber-Optic Biosensors Based on Fluorescence Energy Transfer", Meadows et al., Talanta, vol. 35, No. 2, pp. 145-150, 1988.

"Chemiluminscent and Fluorescent Probes for DNA Hybridization Systems", Heller et al., DNA Hybridization Systems, pp. 245-257 (1985).

"Detection of Nucleic Acid Hybridization by Nonradiative Fluorescence Resonance Energy Transfer", Cardullo et al., Proc. Natl. Acad. Sci. U.S.A., vol. 85, pp. 8790-8794, Dec. 1988.

"Affinity Sensor: A New Technique for Developing Implantable Sensors for Glucose and Other Metabolites", Schultz et al., Diabetes Care, vol. 5, No. 3, pp. 245-253 (1982).

* cited by examiner

ASSAY AND METHOD FOR ANALYTE SENSING BY DETECTING EFFICIENCY OF RADIATION CONVERSION

CROSS-REFERENCE TO RELATED APPLICATIONS

This application claims priority to: U.S. Provisional Application Ser. No. 60/438,490, entitled "Device and Method for Analyte Sensing", filed Jan. 7, 2003. The contents of this provisional application are incorporated by reference herein in its entirety.

BACKGROUND OF THE INVENTION

1. Field of Invention

This invention is directed to a method and an apparatus to facilitate minimally invasive measurement, sampling and/or sensing of analytes, for example, glucose, in a fluid, matrix or animal body.

2. Description of the Related Art

Glucose sensing is an important diagnostic tool in therapy and research of diabetes mellitus as well as in cell culture and on-line process control in agricultural applications. Diabetes is a chronic systemic disease characterized by disorders in the metabolism of insulin, carbohydrate, fat, and protein as well as in the structure and function of blood vessels. Currently, diabetes is a leading cause of death in the United States, and more than sixteen million Americans are believed to have this disease. Intensive management of blood sugars through frequent monitoring is effective to prevent, or at least manage, the progression of diabetic complications such as kidney failure, heart disease, gangrene, and blindness.

Maintaining blood glucose levels near normal levels is typically achieved by frequently monitoring the blood glucose. Currently, the most common method of sensing is a colorimetric/electro-enzymatic approach, which is an invasive technique. In short, the colorimetric/electro-enzymatic approach requires blood to be drawn and tested. This often requires a finger stick to draw blood each time a reading is needed. In sum, this approach is typically time-consuming and often quite painful.

Minimally invasive approaches based on needle-type enzyme sensors (e.g., glucose oxidase) have been investigated as a less painful method of estimating and/or indirectly measuring blood glucose concentrations. Such approaches, however, have well-known limitations regarding measurement of glucose in interstitial fluid. For example, such approaches often suffer from a limitation on the accuracy and stability of the glucose measurement. In this regard, the chemical instability and/or external biocompatibility issues tend to adversely affect the signal sensitivity and stability of the sensor over time. Further, such techniques often require transcutaneous placement of the sensor which may be inconvenient, uncomfortable, a potential source of infection that may ultimately lead to a limitation on the maximum useful lifetime for the sensor. As such, there exists a need for a minimally invasive approach that overcomes one, some or all of the well-known limitations.

SUMMARY OF THE INVENTION

There are many inventions described and illustrated herein.

In one aspect, the present invention is a system, a device and a method for sensing the concentration of an analyte in a fluid or matrix. The analyte may be glucose or any other chemical of interest. The fluid or matrix may be, for example, the fluid in a bioreactor, a food or agricultural product, any fluid or matrix in the body of an animal, or any other fluid or matrix whose concentration of an analyte is under investigation.

In one embodiment, the analyte sensing device includes a housing having an interior space. Contained within the housing and in the interior space is one or more analyte sensing component(s). The analyte sensing component, in one embodiment, includes one or more radiation converting element(s), for example, converting chromophores. The radiation converting element(s) are capable of converting or modifying radiation of one or more wavelengths into radiation of one or more different wavelengths. The conversion efficiency of the radiation converting element(s) is at least partially dependent on the local concentration of an analyte within the analyte sensing component.

The housing may be formed from many different types of materials which are capable of confining, retaining and/or maintaining the analyte sensing component(s) as well as facilitating transmission of at least a portion of radiation incident thereon and originating from within the interior of the housing. At least a portion of the housing includes or is made from a material or materials capable of communicating (e.g., selectively communicating) with the surrounding fluid or matrix so that the analyte of interest may move into and/or out of the interior of the housing while the analyte sensing component(s) may not. In one embodiment, the entire housing is made from such a material.

An analyte sensing system including the analyte sensing device may also include a radiation providing unit to provide radiation of one or more wavelengths to the radiation converting element(s). The system may also include a radiation detecting unit which is capable of detecting radiation that has been converted by the radiation converting element(s).

In another aspect, the present invention is a method of analyte sensing including: providing radiation of one or more wavelengths to a sensing device, detecting a portion of the radiation which has been converted to radiation of one or more different wavelengths, relating the detected converted radiation to a detected efficiency of radiation conversion, and determining the analyte concentration based on the detected efficiency of radiation conversion.

Again, there are many inventions described and illustrated herein. By no means is this Summary exhaustive of the scope of the present invention. Moreover, this Summary is not intended to be limiting of the invention and should not be interpreted in that manner. While certain embodiments, features, attributes and advantages of the inventions have been described here, it should be understood that many others, as well as different and/or similar embodiments, features, attributes and/or advantages of the present inventions, which are apparent, for example, to those skilled in the art, from the description, examples, illustrations and claims—all of which follow.

BRIEF DESCRIPTION OF DRAWINGS

In the course of the detailed description to follow, reference will be made to the attached drawings. These drawings show different aspects of the present invention and, where appropriate, reference numerals illustrating like structures, components, materials and/or elements in different figures are labeled similarly. Various combinations of the structures, components, materials and/or elements, other than those specifically shown, are contemplated and are within the scope of the present invention.

DETAILED DESCRIPTION

There are many inventions described and illustrated herein. In one aspect, the present invention is a system, a device and a method for sensing the concentration of an analyte (e.g., glucose) in a fluid or matrix (e.g., the fluid in a bioreactor, a food or agricultural product, or animal body). In one embodiment, the analyte sensing device includes an analyte sensing component, including a plurality of radiation converting components that are in contact with the fluid or matrix and are capable of converting radiation of one or more wavelengths into radiation of one or more different wavelengths. The conversion efficiency(ies) of the radiation converting components is at least partially dependent on the concentration of an analyte within the fluid or matrix.

Figure 1A:
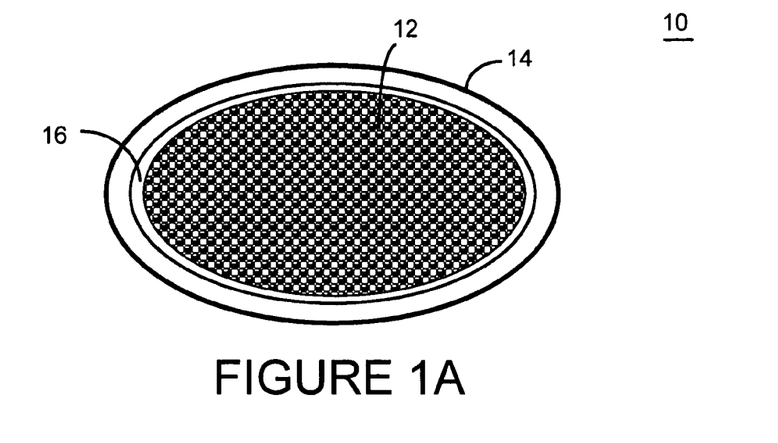
FIG. 1A is a schematic representation of a portion of an analyte sensing device, according to one embodiment of the present invention.
Figure 1B:
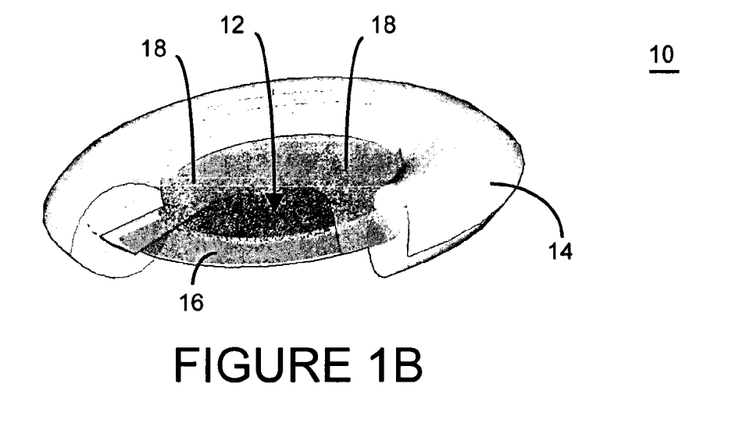
FIG. 1B is a three-dimensional illustration (with a portion cut-away) of an analyte sensing device according to one embodiment of the present invention.
Figure 1C:
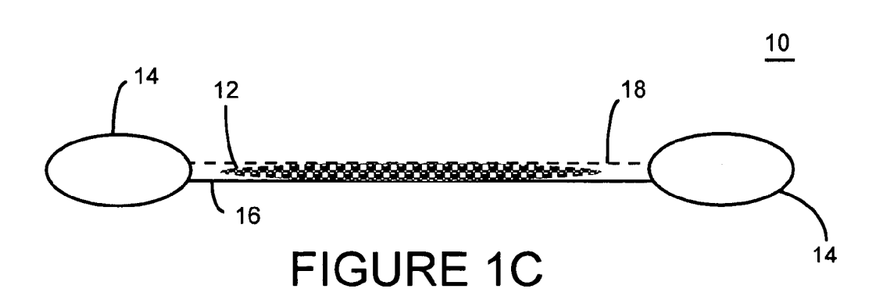
FIG. 1C is a cross-sectional view of an analyte sensing device illustrated in FIG. 1B according to one embodiment of the present invention.

With reference to FIGS. 1A–1C, in one embodiment, analyte sensing device 10 includes at least one analyte sensing component 12 and housing 14. The analyte sensing component 12 is employed to measure, sense and/or detect the concentration of analyte under investigation by converting at least a portion of incident radiation (provided by a radiation providing unit) having one or more wavelengths to converted radiation, which is radiation of one or more different wavelengths.

The housing 14, in one embodiment, is comprised of base 16 and membrane 18. The base 16 provides a support for analyte sensing device 10 in order to generally maintain its shape over time. The base 16 may be constructed from a material that is impermeable to fluid, for example, the fluid under investigation. In one embodiment, base 16 may include a biocompatible material, for example, cured silicone or a polymer material treated to render its surface compatible with biological tissue. Such treatment may consist of, for example, so-called pegylation, whereby poly (ethylene glycol) (PEG) polymers known to be biocompatible are attached to the material surface.

The membrane 18 allows fluid or analyte communication between analyte sensing device 10 and the fluid (and/or the analyte contained therein) under investigation. In one embodiment, membrane 18 facilitates equilibration between an external analyte concentration and an internal analyte concentration by allowing analyte to cross the material boundary of analyte sensing device 10. The membrane 18 may be constructed from a material that is permeable or semi-permeable (e.g., a cellulose acetate membrane)

The analyte sensing component 12 is maintained within analyte sensing device 10 via housing 14. That is, housing 14, and, in particular, membrane 18 confines analyte sensing component 12 within analyte sensing device 10. In addition, as mentioned above, membrane 18 facilitates fluid/analyte communication between analyte sensing component 12 and the analyte within the fluid under investigation.

Notably, analyte sensing device 10 may include housing 14 comprised of, in certain embodiments, a semi-permeable housing material. For example, housing 14 may be made from a hollow dialysis fiber made of cellulose acetate. In addition, housing 14 may also be constructed of polyurethane, polyethylene, or polysulphone.

Figure 2:
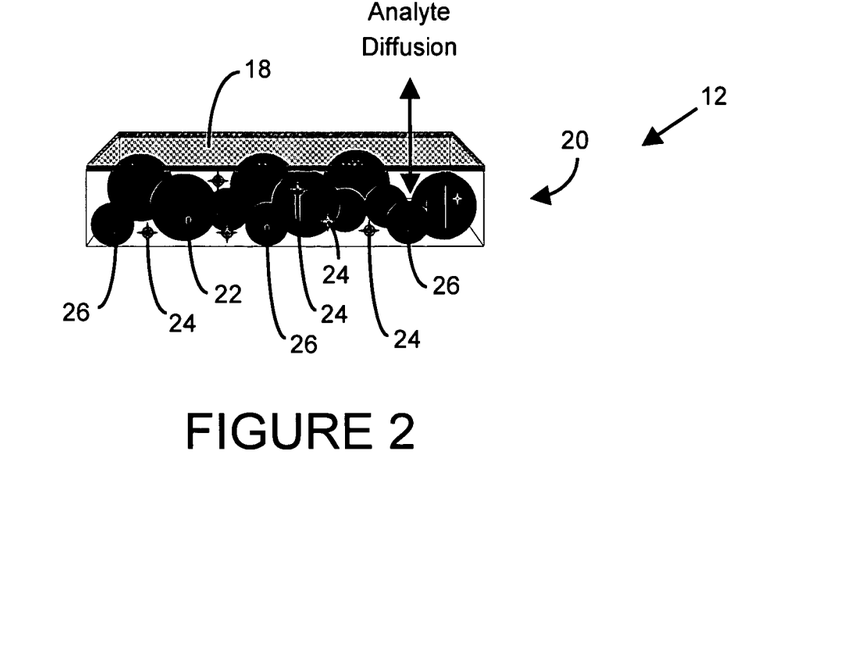
FIG. 2 is a three-dimensional schematic representation of a portion of the analyte sensing component according to at least one embodiment of the present invention.

With reference to FIG. 2, in one embodiment, the analyte sensing component 12 includes macroporous matrix layer 20 having analyte-specific binding ligand 22 (for example, lectin such as Concanavalin A or *Lens culinaris* lectin). The analyte-specific binding ligand 22 may be bound to the surface of the macroporous matrix layer 20 and/or may be embedded throughout macroporous matrix layer 20.

Where the analyte of interest is glucose, macroporous matrix layer 20 may include a plurality of porous agarose beads (e.g., Sepharose(™) having a mean diameter of between 10–100 micrometers). Moreover, in this example, analyte-specific binding ligand 22 may be Concanavalin A (ConA), which is a lectin generally known to bind glucose and similar sugars.

The analyte-specific binding ligand 22, in one embodiment, is covalently labeled with or is in close proximity to an absorbing chromophore capable of absorbing radiation. In one embodiment, radiation absorbing chromophore may be, for example, QSY-21™ which exhibits a broad optical radiation absorption peak extending from 650 nm to 750 nm. Notably, any radiation absorbing chromophore, whether now known or later developed, is intended to be within the scope of the present invention. Indeed, as described in detail below, the radiation absorbing chromophore may be selected in accordance with other aspects of analyte sensing component 12.

The analyte sensing component 12 also includes an analyte-analogue covalently labeled with first radiation converting chromophore 24. In one embodiment, the analyte-analogue, may be, for example, dextran which is a polymeric chain of glucose residues and may also be bound by analyte-specific binding ligand 22, for example, the lectin ligand ConA. The first radiation converting chromophore 24 may be, for example, ALEXA647™, which is capable of converting optical radiation between 630–650 nm into optical radiation between 650–750 nm.

In another embodiment, the analyte-analogue, may be, for example, glycosylated, mannosylated protein and/or mannosylated dendrimer.

The analyte sensing component 12 may also include second radiation converting chromophore 26. The second radiation converting chromophore 26 may be, for example, LD800™, which is capable of converting optical radiation between 630–650 nm into optical radiation between 700–750 nm. The second radiation converting chromophore 26 may also be a system of chromophores embedded in beads (e.g. TransFluoroSpheres(™)) which is capable of converting optical radiation between 620–650 nm into optical radiation between 750–760 nm. Indeed, second radiation converting chromophore 26 may be included or incorporated into macroporous matrix layer 20 as beads or particles embedded within macroporous matrix layer 20.

With reference to FIGS. 1A–1C, 2 and 3, in operation, a system according to one embodiment of the present invention includes analyte sensing device 10, radiation providing unit 28, radiation detecting unit 30 and analyte concentration analysis unit 32. Briefly, by way of overview, radiation providing unit 28 provides transmitted radiation 34 (e.g., optical radiation having a first wavelength or wavelengths) to analyte sensing device 10. In response to transmitted radiation 34, which is incident thereon, analyte sensing device 10 converts at least a portion of the radiation of the first wavelength(s) to radiation having another or different wavelength(s). In this regard, transmitted radiation 34 impinges upon analyte sensing component 12 (having the analyte sensing chemistry) and at least a portion of the radiation is converted to radiation of a different wavelength(s). The radiation detecting unit 30 measures, senses, detects and/or samples radiation 36 and outputs data (analog or digital) which is representative thereof. The analyte concentration analysis unit 32 uses that data to determine, calculate, assess and/or detect the concentration of analyte in the fluid under investigation.

Figure 3:
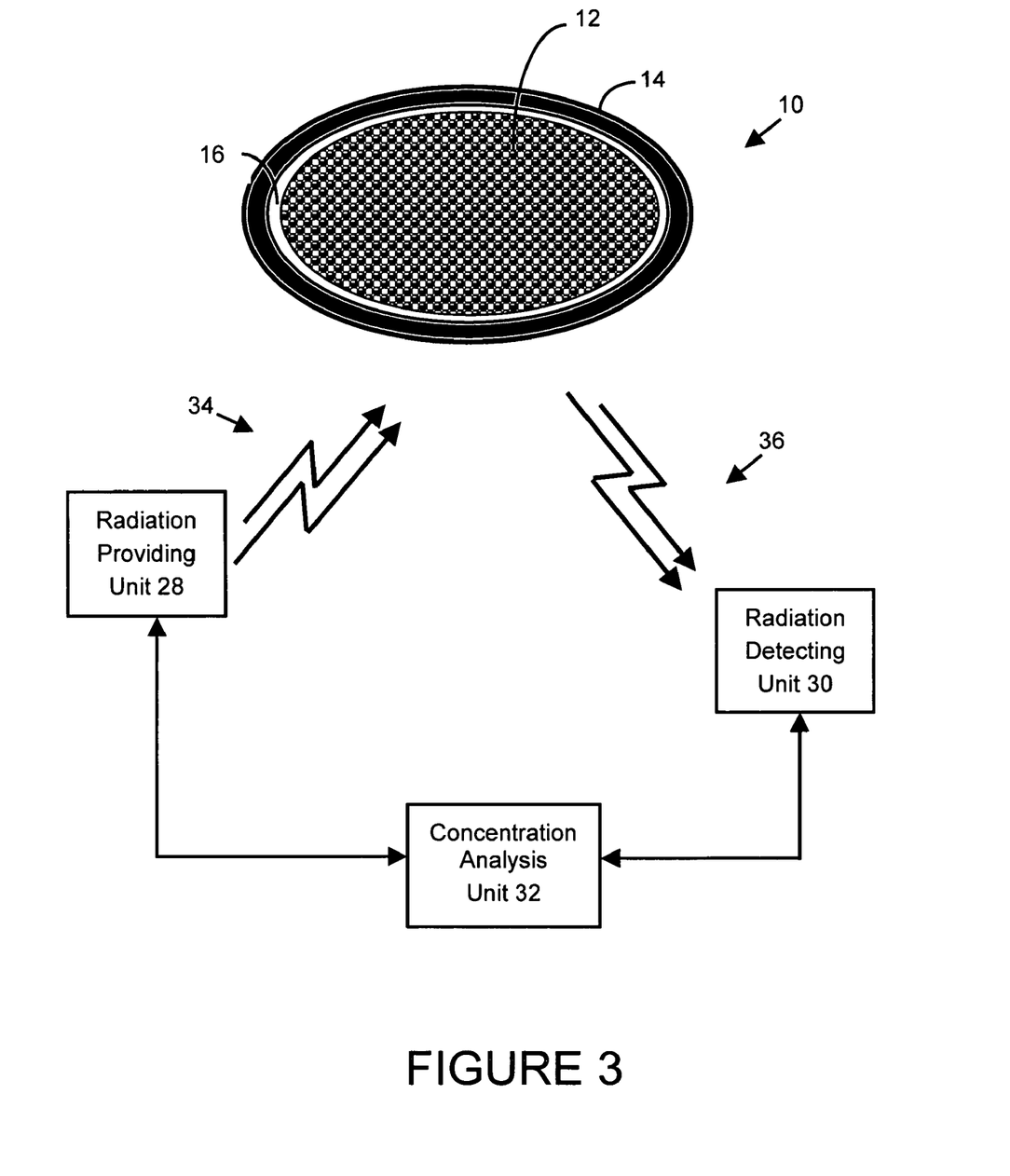
FIG. 3 is a schematic representation of a portion of an analyte sensing device of FIG. 1, in conjunction with the radiation providing unit and radiation detecting unit.

In one embodiment, for example, radiation providing unit 28 may include, for example, a laser operating at a wavelength between 630–650 nm. As such, the transmitted radiation includes energy having a wavelength between 630–650 nm. Indeed, in at least one embodiment, the laser provides optical radiation having a wavelength of 645 nm.

In one embodiment, the incident energy having a wavelength between 630–650 nm may be converted and/or modified to an optical radiation having a wavelength of approximately 675 nm. In this regard, a portion of transmitted radiation 34 is converted and/or modified by the first radiation converting chromophore 24 that is, for example, unbound or bound to analyte-specific binding ligand 22. At least a portion of the converted and/or modified transmitted radiation 34 (i.e., modified radiation 36), is transmitted through housing 14 and received, sensed, sampled, detected and/or measured by radiation detecting unit 30.

In one embodiment having a plurality of radiation converting chromophores, the modified radiation 36, in addition emitting optical radiation having a wavelength of approximately 675 nm, may also include a component of optical radiation having a wavelength of approximately 725 nm. The radiation of the second wavelength may be which is generated by second radiation converting chromophore 26 and which is transmitted through housing 14. In this embodiment, radiation detecting unit 30 senses, samples, detects and/or measures at least a portion of the modified or converted radiation 36 that is transmitted through housing 14.

The radiation detecting unit 30 may include optics and electronics to sense, sample, detect and/or measure radiation having one or more wavelengths. For example, in the embodiment including second radiation converting chromophore (i.e., beads or particles 26), radiation detecting unit 30 may sense, sample, detect and/or measure modified or converted radiation 36 which includes energy having at least two wavelengths.

Alternatively, or in addition thereto, radiation detecting unit 30 may include a plurality of radiation detecting devices, each device being capable of sensing, sampling, detecting and/or measuring a wavelength-specific portion of the modified or converted radiation 36 (e.g., the wavelength of the radiation generated, converted and/or modified by first chromophore, or the intensity of radiation generated, converted and/or modified by first chromophore).

The radiation detecting unit 30 may include, for example, one or more photodiode detectors and wavelength specific optical filters. The radiation detecting unit may also be, for example, a charge-coupled device (CCD) array and a dispersive unit (i.e. a spectrograph), not illustrated. The radiation detecting unit 30 may also be combinations or permutations thereof, or may include other instrumentation for detecting converted or modified radiation 36. Indeed, any and all techniques and/or devices to measure converted or modified radiation 36, whether now known or later developed, are intended to be within the scope of the present invention.

Notably, radiation providing unit 28 and/or the radiation detecting unit 30 may be located inside of, or adjacent to, housing 14 of analyte sensing device 10. Radiation providing unit 28 and/or the radiation detecting unit 30 may also be integrated into housing 14 of analyte sensing device 10 as a more self-contained device.

In the illustrated embodiment, the amount of converted radiation 36 sensed, sampled, detected and/or measured by radiation detecting unit 30 may depend upon, for example: (i) the amount of transmitted radiation 34 which is incident on and/or reaches the radiation converting chromophore(s) 24 and/or 26 (which in turn depends on the intensity of transmitted radiation 34 provided by radiation providing unit 28); (ii) the efficiency of the "delivery" to device 10, and the transmissivity of housing 14; (iii) the conversion efficiency of radiation converting chromophore(s) 24 and/or 26; and (iv) the efficiency with which the converted radiation 36 is transmitted back to radiation detecting unit 30 (which depends in part on the transmissivity of housing 14 to the converted radiation 36, the efficiency of transmission of converted radiation 36 to radiation detecting unit 30, and the physical arrangement of radiation detecting unit 30 with respect to analyte sensing device 10).

In at least one embodiment of the present invention employing at least two radiation converting chromophores, the first and second converting chromophores 24 and 26 are chosen so that all elements of (i) through (iv) are the same or substantially the same for each wavelength of converted radiation 36. In this way, differences in the relative amounts of detected radiation of the first and second wavelengths detected by radiation detecting unit 30 depend, to a significant extent, on the conversion efficiency of each of the radiation converting chromophores 24 and 26.

In another embodiment of the present invention employing at least two converting chromophores, first converting chromophore 24 is selected, chosen and/or designed to include an adjustable or modifiable conversion efficiency, which is altered, changed and/or adjusted by the concentration of analyte under investigation. However, in this embodiment, second converting chromophore 26 is selected and/or designed to include a conversion efficiency which is independent (or substantially independent) of the concentration of analyte under investigation. In this way, the change in conversion efficiency, which is dependent on the concentration of analyte, may be more readily deduced by comparing the amount of detected radiation of the first wavelength(s) and the amount of detected radiation of the second wavelength(s).

In one embodiment, analyte sensing component 12 may be realized when the conversion efficiency of the first radiation converting chromophore 24 is dependent upon its physical or spatial proximity to an absorbing chromophore within macroporous matrix layer 20. The first radiation converting chromophore 24 may be chosen such that, when the radiation converting chromophore is spatially located in close proximity to absorbing chromophores, a portion of the energy which would be otherwise transmitted and/or released as converted radiation by chromophore 24 is "leaked" to, "captured" by, and/or absorbed by the absorbing chromophores. In this way, the conversion efficiency of the radiation converting chromophore is decreased, and the detected first converted radiation will be of lesser amount.

Since the analyte-specific binding ligand 22 is capable of binding the analyte-analogue containing radiation converting chromophore 24, and since the absorbing chromophore is bound to or near to the analyte-specific binding ligand 22, the first radiation converting chromophore 24 may be in close spatial proximity to the absorbing chromophore, and its conversion efficiency concomitantly decreased. As such, in the absence of analyte, the number of analyte binding sites available to analyte-analogue is increased, and therefore, there is a higher probability that a particular first converting chromophore 24 has its conversion efficiency decreased. In the presence of analyte, certain of the analyte binding sites will be occupied by analyte, and, as such, there is a lower probability that analyte-analogue will be bound to analyte binding ligand 22. It follows that the probability that a particular first converting chromophore 24 will be in close proximity to an absorbing chromophore will decrease. Therefore, the apparent average conversion efficiency of radiation converting chromophore 24 will increase in the presence of the analyte under investigation.

As mentioned above, analyte concentration analysis unit 32 uses the data output by radiation detecting unit 30 to determine, calculate, assess and/or detect the concentration of analyte in the fluid under investigation. In this regard, the analyte concentration analysis unit 32 employs well-known techniques. For example, in one embodiment, analysis unit may compute the ratio of the intensity of converted radiation in a first wavelength range (corresponding to radiation from the first radiation converting chromophore 24) to the intensity of converted radiation in a second wavelength range (corresponding to radiation from the second radiation converting chromophore 26). Further, analysis unit 32 may first condition the signal(s) received from radiation detecting unit 30 prior to performing other calculations. Such conditioning may include, for example, normalization, base-line correction, or removal of other sources of interference from the data.

Notably, other techniques, devices and/or systems may be implemented to realize an analyte concentration dependent change in radiation conversion efficiency. For example, the first radiation converting chromophore 24 may be bound to the analyte binding ligand 22, and the analyte-analogue may be bound to or near the absorbing chromophore. In this case, in the absence of analyte, the analyte binding ligand 22 will be bound to the analyte-analogue, and a concomitant decrease in detected conversion efficiency by the first radiation converting chromophore 24 will result. Conversely, when analyte is present, it will occupy the binding sites on the analyte binding ligand 22 and free it from the analyte-analogue, resulting in an increase the detected radiation conversion efficiency. Note in particular, that the analyte-analogue may be bound to or near to or embedded throughout a macroporous matrix material. As well, the analyte-analogue may comprise, at least in part, the macroporous matrix, and may be, for example, Sephadex(™).

Figure 4:
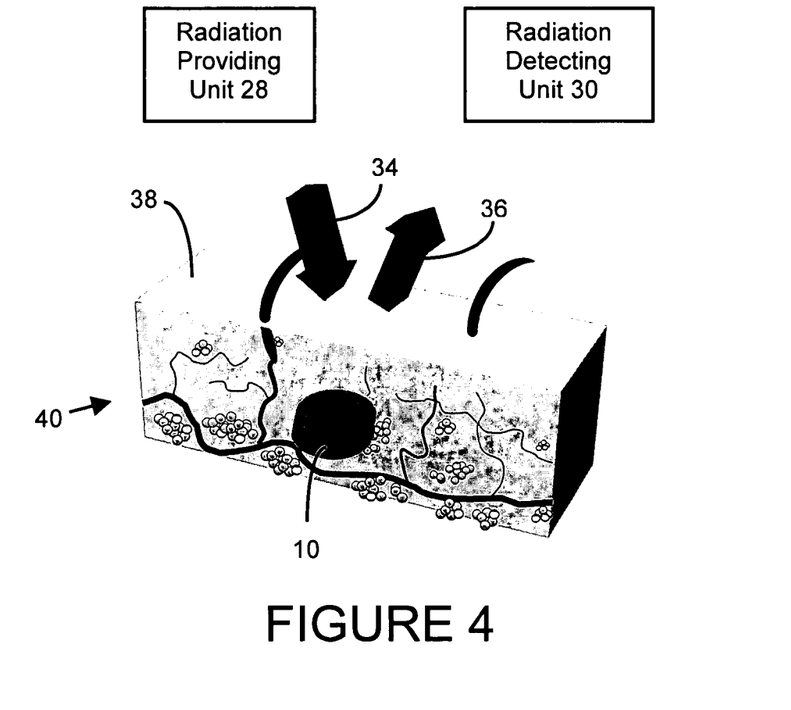
FIG. 4 is a three-dimensional cross-sectional illustration of an analyte sensing device, embedded in an animal body, according to one embodiment of the present invention.

With reference to FIG. 4, in one embodiment, analyte sensing device 10 may be implanted under skin surface 38 of an animal body. It will be appreciated that analyte sensing device 10 may be any of the embodiments described herein. The sensing device 10 may be implanted into the skin tissue 40 of an animal body and resides in a location of tissue matrix where at least a portion of the sensing device is in communication with blood or interstitial fluid. The analyte of interest which is present in the surrounding body tissue, fluid, or matrix (e.g., interstitial fluid or blood) may enter device 10 in amounts proportional to the concentration of the analyte in the surrounding body tissue fluid or matrix.

Attenuation or alteration of the transmission of both transmitted and detected converted radiation may be caused by skin, body tissues, and/or fluids, as well as previously described factors. As such, converting chromophore(s) 24 and/or 26 may be chosen so that these effects are the same or substantially the same for the wavelength(s) of the converted or modified radiation 36. Thus, where analyte sensing device 10 includes first and second radiation converting chromophore(s) 24 and/or 26, the difference in detected amounts of the analyte-sensitive first converted radiation and the analyte-insensitive second converted radiation may be related to the concentration of analyte surrounding analyte sensing component 12.

While a technique of compensating for attenuation or loss of transmitted radiation and converted radiation has been described above, in one embodiment, it may be advantageous to employ first radiation converting chromophore 24 and/or second radiation converting chromophore 26 that emit, generate, modify and/or convert the radiation of the transmitted wavelength(s) to a radiation spectrum which is particularly well transmitted by skin, other body tissues and/or fluids. The spectral region composed of very near-infrared optical radiation is one such portion of the radiation spectrum. For example, the first and/or second converting chromophore may be ALEXA647™ (Molecular Probes, Inc.), ALEXA680™ (Molecular Probes, Inc.), ALEXA690™ (Molecular Probes, Inc.), TransFluoSpheres™ (Molecular Probes, Inc.), and/or LD800™ (Exciton, Inc.).

Notably, in selecting or choosing first radiation converting chromophore 24 and/or second radiation converting chromophore 26, a corresponding absorbing chromophore may also be selected which is capable of altering the conversion efficiency of the radiation converting chromophore. For example, converting and absorbing chromophore pairs in the radiation portion of interest may be: ALEXA633™/ QSY21™, CY5™/QSY21™, ALEXA647™/QSY21™, ALEXA647™/ALEXA680™, ALEXA680™/allophycocyanin (APC), ALEXA700™/APC, and/or ALEXA750™/ APC (Molecular Probes, Inc.). It is contemplated, however, that any suitable pair of first and/or second radiation converting chromophore and radiation absorbing chromophore, whether now known or later developed, is within the scope of the present invention.

Figure 5A:
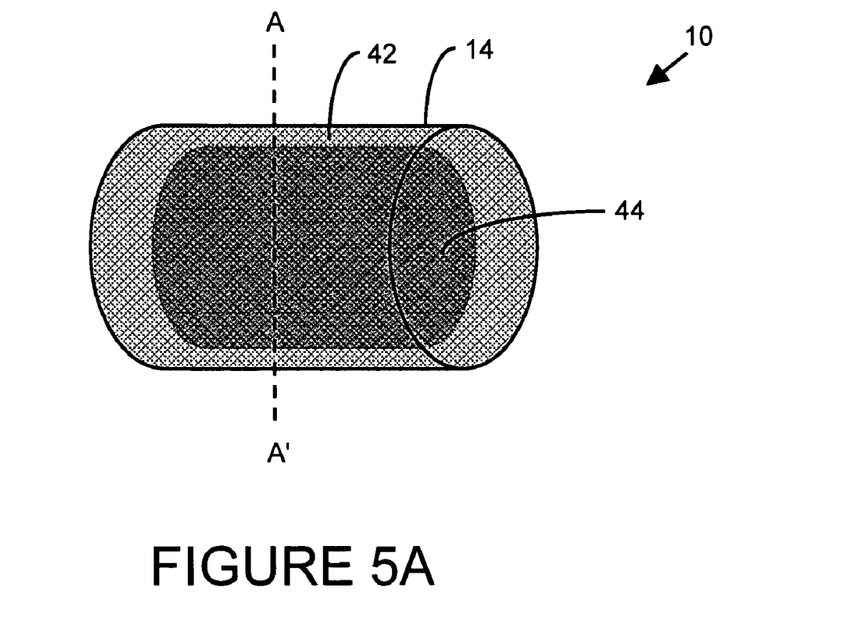
FIGS. 5A and 5B (which is a cross-section of FIG. 5A along lines A–A') are illustrations of an analyte sensing device according to another embodiment of the present invention wherein the analyte sensing device includes a polymer encapsulation material.
Figure 5B:
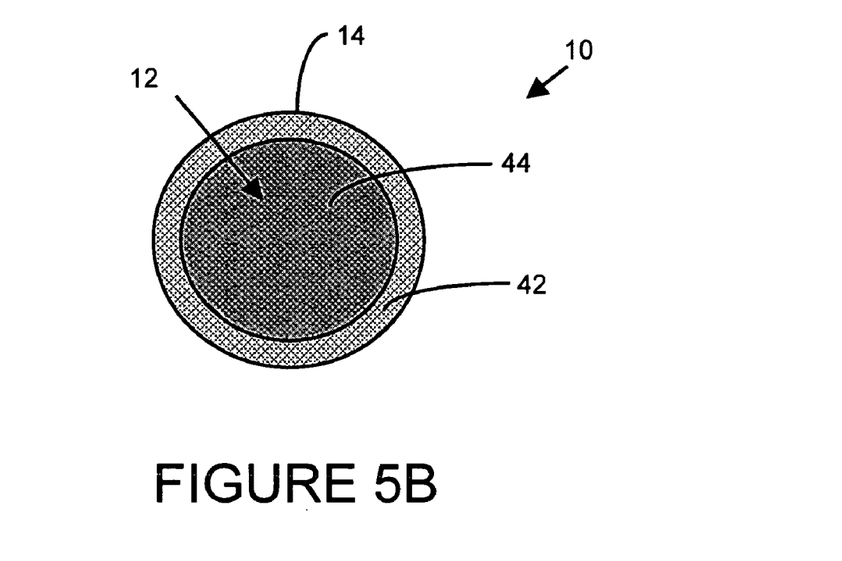

With reference to FIGS. 5A and 5B, in one embodiment of the present invention, analyte sensing component 12 may be contained within polymeric matrix 42. In such an embodiment, housing 14 may also be comprised of a polymer (hereinafter, polymeric housing 14) and include a permeable or semi-permeable capsule 44 which contains, maintains and/or retains the analyte sensing chemistry (i.e., analyte sensing component 12) while allowing analyte concentration within the surrounding fluid to vary by free movement of analyte into and out of semi-permeable capsule 44. The polymeric housing 14 may selectively or entirely surround polymeric matrix 42 containing analyte sensing component 12. Alternatively, analyte sensing component 12 may be embedded throughout polymeric matrix 42 formed by or comprised of the material of the polymeric housing 14.

It may be advantageous to employ a polymeric housing 14 that is permeable to the analyte of interest and that also permits movement or motion of ligands and analyte-analogues within the interior of permeable or semi-permeable capsule 42 without permitting the ligands and analyte-analogues to "escape" housing 14. For example, polymeric housing 14 may be comprised of poly(ethylenelgycol) (PEG) and/or synthetic derivatives thereof, calcium phosphate, polyurethane, alginate, regenerated cellulose acetate, chitosan, or combinations thereof. Moreover, it may be advantageous to employ polymers having cross-linking density, porosity and/or swelling properties that may be adjusted, modified and/or tailored to meet or address, for example, the environmental requirements of analyte sensing device 10. Notably, techniques for adjusting such properties are well known to those skilled in the art.

The housing 14 may be constructed from one or more discrete polymeric formulations to provide the desired properties. For example, analyte sensing device 10 may be constructed of polymeric matrix 42 containing analyte sensing component 12 and forming a core around which a second more dense polymeric capsule 42 is formed. (See, for example, FIGS. 5A and 5B).

Figure 6A:
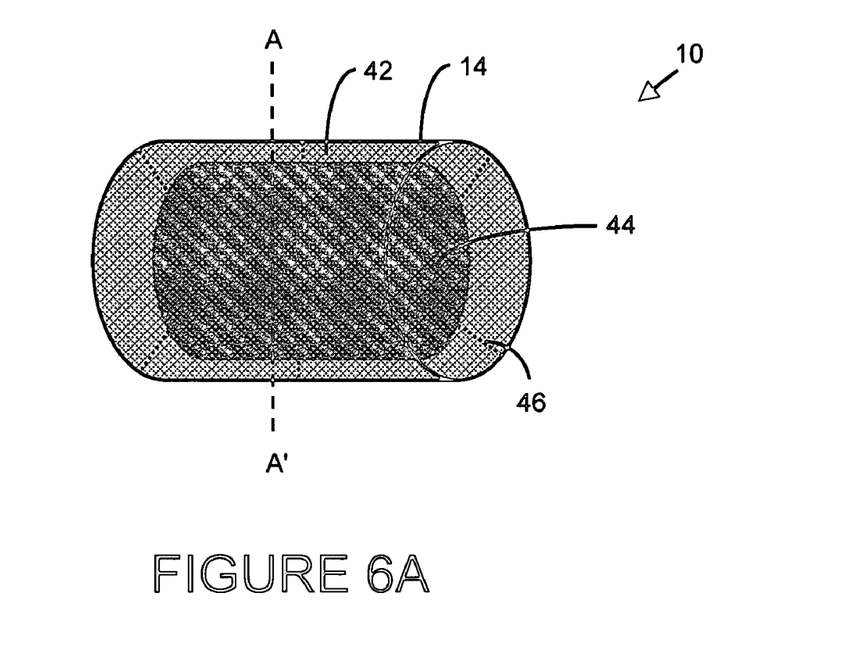
FIGS. 6A and 6B are illustrations of an analyte sensing device according to another embodiment of the present invention wherein the analyte sensing device includes a polymer encapsulation material and covalent linkages suspending the analyte sensing component(s)
Figure 6B:
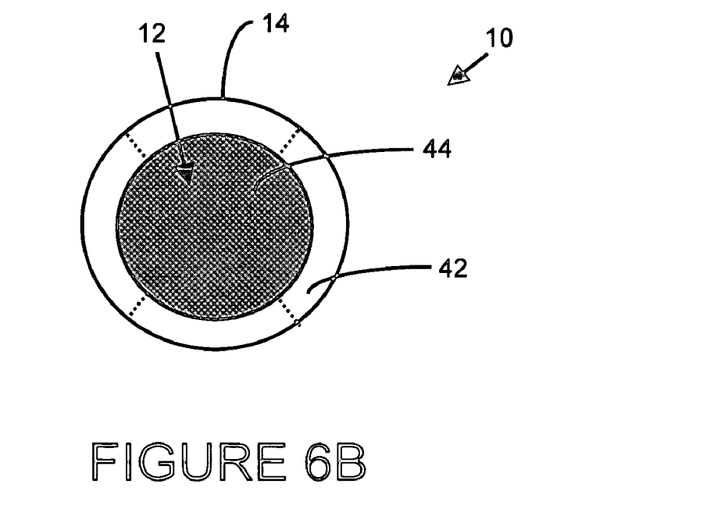

Further, with reference to FIGS. 6A and 6B, analyte sensing component 12 may be retained in the interior of polymeric housing 14 via covalent linkages 46 to the polymeric backbone chains themselves. In this way, components of the analyte sensing component would be "tethered" to polymeric housing 14 and free to move inside, but not to "escape". The analyte would still be free to communicate into and out of polymeric housing 14 and to interact with analyte sensing component 12.

As mentioned and illustrated above, analyte sensing device 10 may be implanted into the tissues of the body of an animal. Such implantation may be accomplished by making a small incision in skin surface 38 and skin tissue 40 into which analyte sensing device 10 may be inserted, implanted, disposed, placed and/or affixed. Indeed, any technique for inserting, implanting, disposing, placing and/ or affixing analyte sensing device(s) 10 into the animal body, whether now known or later developed, are intended to be within the scope of the present invention.

For example, in those embodiments where analyte sensing device 10 may be contained in a hypodermic needle, analyte sensing device 10 may be implanted into skin tissue 40 by pushing it through the hypodermic needle which is inserted under the skin surface 38. For example, in the case where analyte sensing device 10 includes a housing of a polymer matrix, the external diameter of the particles may be made sufficiently small as to allow their injection. For example, one or a plurality of polymer spheres or particles roughly 1–500 µm in diameter may be collected and injected into or underneath the skin or other desirable body location.

Figure 11:
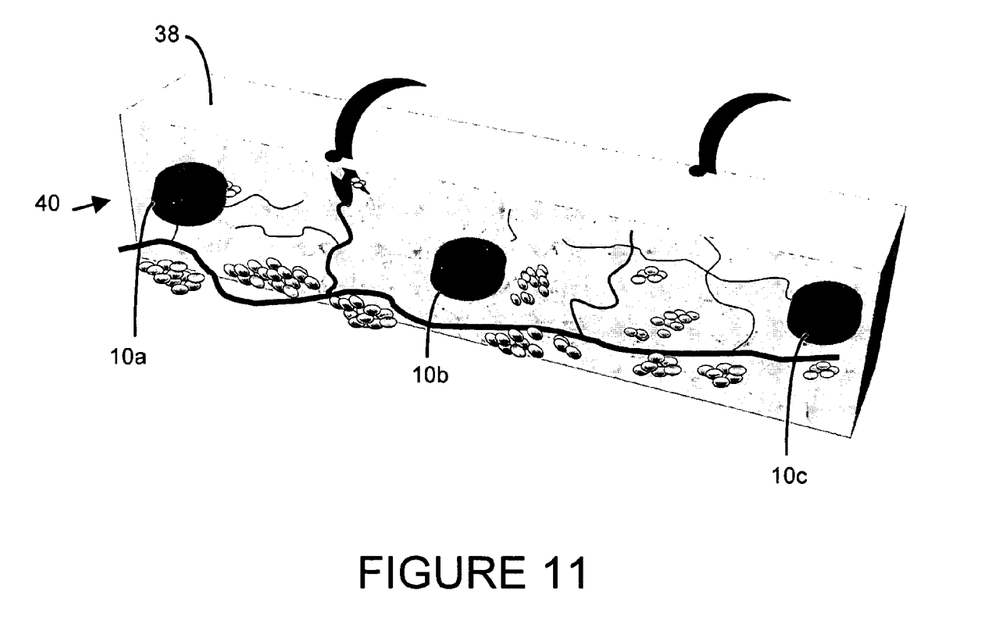
FIG. 11 is a three-dimensional cross-sectional illustration of a plurality of analyte sensing devices, embedded in an animal body, according to one embodiment of the present invention.

Notably, in one embodiment, one or more analyte sensing devices 10 may be inserted, implanted, disposed, placed and/or affixed by subcutaneous or intradermal injection. In this way, a number of locations of the body may be assessed and/or a gradient may be determined. (See, for example, FIG. 11).

Figure 7:
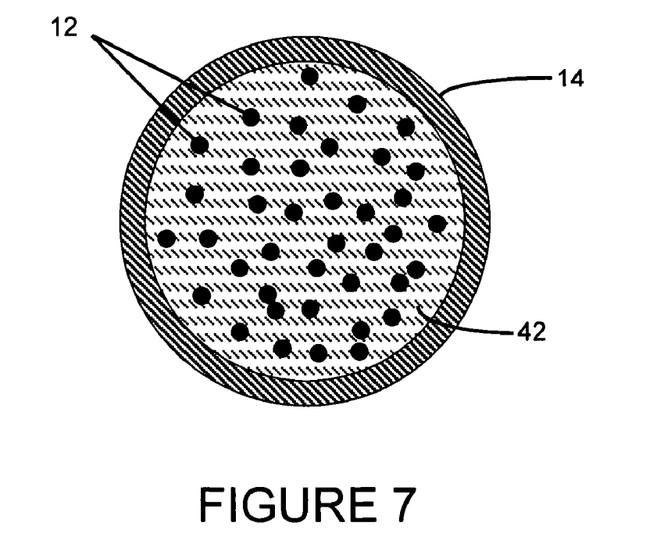
FIG. 7 is an illustration of an analyte sensing device according to another embodiment of the present invention wherein the analyte sensing device includes a dual polymer encapsulated material.

In at least one embodiment of the present invention, analyte sensing device 10 may be formed in situ. That is, a liquid precursor may be injected into or under skin surface 38 and thereafter a polymeric housing is formed from the liquid precursor. In this embodiment, the liquid precursor includes, for example, macroporous matrix layer 20, analyte-specific binding ligand 22, first converting chromophore (e.g., sepharose beads) 24, and/or second converting chromophore (e.g., beads or particles) 26. For example, analyte sensing device 10 of this embodiment may be formed using transdermal (through skin surface 38) photo initiated cross-linking polymerization. In such an embodiment, the liquid precursor consists of analyte sensing components 12 mixed or co-dissolved with a polymer precursor solution. The analyte sensing components 12 may be free in the solution, or may be already covalently tethered to a portion of the monomer in the precursor mixture. (See, for example, FIG. 7).

Further, the polymer precursor solution may contain unlinked monomer and a photoinitiator which initiates cross-linking of the monomers subsequent to activation by suitable optical radiation. For example, a PEG-diacrylate or PEG-dimethacrylate monomer may be dissolved in water and co-dissolved with a photoinitiator such as dimethoxyphenyl acetophenone (DMPA) or hydroxyphenyl ketone (HPK), among others. Upon irradiation with light at approximately 365 nm, the photoinitiator forms a free radical which attacks carbon-carbon double bonds in acrylated or methacrylated termini of PEG monomer chains. These attacked sites in turn attack other PEG termini forming stable cross-linked networks of PEG polymer. In this way, photoactivation is used to initiate polymerization of the sensor housing component.

It should be noted that sufficient amount/intensity of radiation having a wavelength in the range of 365 nm may be delivered through skin 38 such that a precursor mixture injected in liquid form may be made to polymerize by providing polymerization initiating radiation from outside the animal body.

Yet another technique for polymerizing analyte sensing device 10 subsequent to injection of the precursor mixture is to utilize a temperature sensitive polymer formulation. Several polymers are well known to those skilled in the art to have very sharp phase transitions over narrow temperature ranges. A polymer which is a solid or gel at body temperature but is a liquid at slightly higher temperatures could be warmed to a liquid and injected into or below the skin. As the precursor then cools, it gels into analyte sensing device 10. (See, for example FIG. 7).

Notably, other techniques of controlling the phase of the polymer may be utilized. It is intended that all techniques and materials, whether now known or later developed are within the scope of the present invention, including, for example, controlling the phase of the polymer via pH dependence.

For rapid sensing of analyte concentration, it may be desirable that the communication of analyte into and out of analyte sensing device 10 be as rapid as possible. The rate of analyte concentration can be enhanced by increasing, for example, the permeability of the semi-permeable portion of housing 14, namely membrane 18. Additionally, the rate of communication may also be enhanced, for example, by increasing the surface area of membrane 18 relative to the fluid under investigation. In those instances where housing 14 is comprised of polymer, the surface-area-to-volume ratio of analyte sensing device 10 may be at least partially impact the rate at which the analyte sensing component 12 may respond to a change in analyte concentration in the fluid under investigation. It may therefore be desirable, for example, to include or employ a plurality of analyte sensing devices 10 and/or components 12 having a small spherical shape rather than a single spheroid of similar total volume. (See, for example, FIGS. 8, 9A and 9B).

Figure 8:
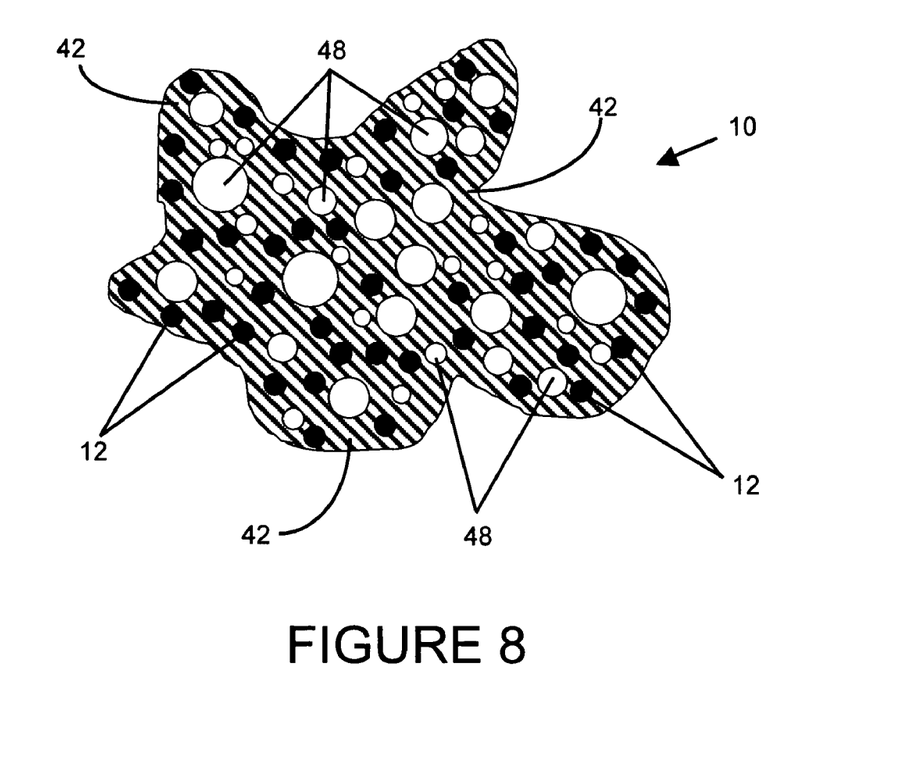
FIG. 8 is an illustration of an analyte sensing device according to yet another embodiment of the present invention wherein the analyte sensing device includes a macroporous polymeric material.
Figure 9A:
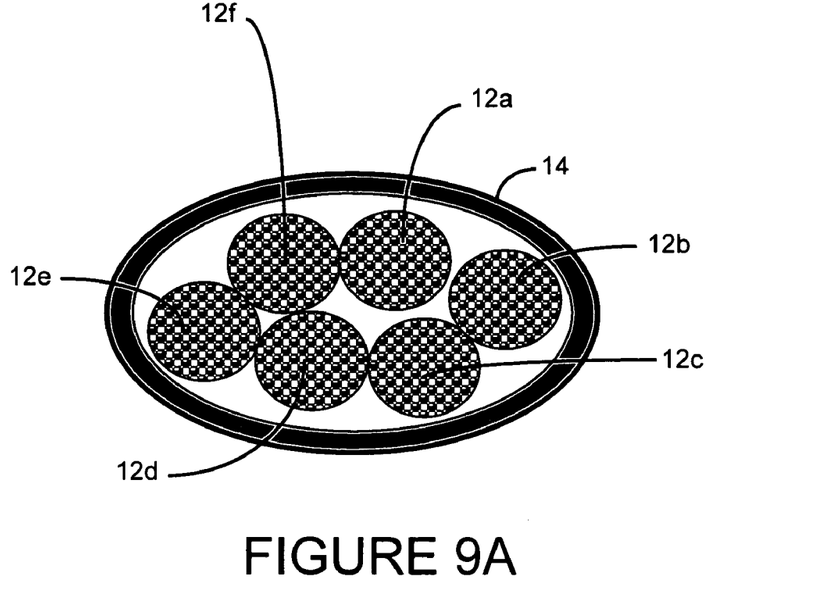
FIGS. 9A and 9B are schematic representations of a portion of an analyte sensing device, according to certain embodiments of the present invention, wherein the sensing device includes a plurality of analyte sensing components.
Figure 9B:
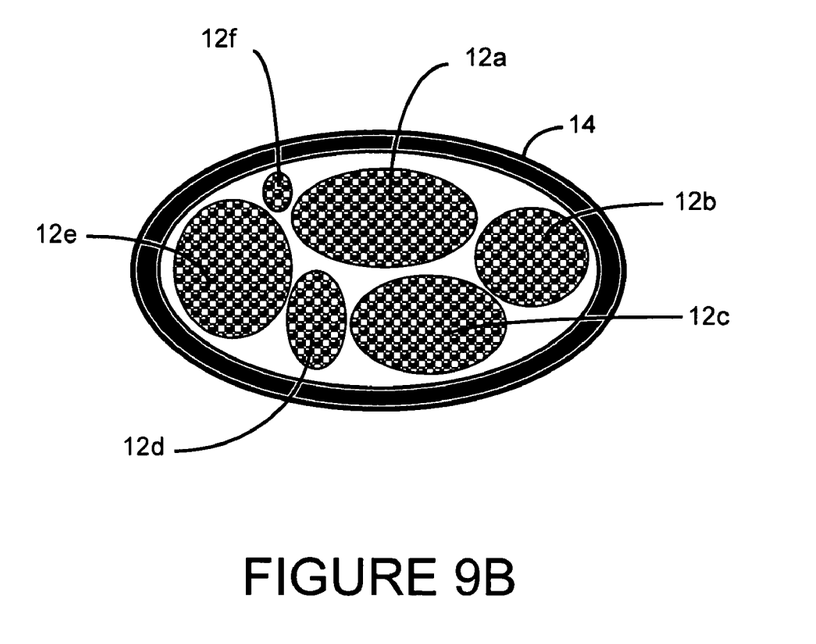

Notably, while illustrated as substantially spherical, analyte sensing device(s) 10 and/or component(s) 12 may have or take any shape. Similarly, in the creation of a polymer from a liquid precursor mixture, it may be desirable to construct analyte sensing device 10 with a large surface area relative to its total volume. At least one way for realizing such a configuration can be accomplished by adding an additional forming component to the precursor mixture. In at least one embodiment, the forming component may be injected with the precursor mixture and acts to increase the surface area of the polymerized sensor. For example, the forming component may be an oil or other liquid which is immiscible in/with the polymer/sensor precursor mixture. By shaking or otherwise agitating the resulting mixture, the phases may form in part or in total an emulsion consisting of small local domains of sensor precursor interspersed with small local domains of the forming component. The resulting emulsion may, for example, take on a "frothy" appearance. Injection and subsequent polymerization of such an emulsion can be made to result in a polymer with a large number of voids and "bubbles" 48 resulting from the presence of the forming agent. If the forming agent is inert and eventually leeches away or is otherwise removed from the resulting polymer sensor structure, a sensor with a highly porous macrostructure and hence highly contorted surface will result. A schematic representation of such an embodiment is illustrated in FIG. 8.

There are many inventions described and illustrated herein. While certain embodiments, features, materials, attributes, structures and advantages of the present inventions have been described and illustrated, it should be understood that many other, as well as different and/or similar embodiments, features, materials, attributes, structures and advantages of the present inventions, are apparent from the description, illustration and claims. As such, the embodiments, features, materials, attributes, structures and advantages of the present inventions described and illustrated herein are not exhaustive, and it should be understood that such other, similar, as well as different, embodiments, features, materials, attributes, structures and advantages of the present inventions are within the scope of the present invention.

For example, analyte sensing device 10 may include a plurality of analyte sensing components 12$a$–$f$. (See, for example, FIGS. 9A and 9B). The analyte sensing components 12$a$–$f$ may be formed into any shape within housing 14. (See, for example, FIG. 9B).

Moreover, analyte sensing device 10 may employ the same or different radiation converting chromophores and/or analyte binding ligands and/or analyte-analogues. That is, in one embodiment, a plurality of radiation converting chromophores may be employed in analyte sensing device 10 where each chromophore generates, changes and/or modifies the radiation to different or the same wavelengths. For example, analyte sensing device 10 may employ a plurality of radiation converting chromophores that convert and/or modify the incident radiation and provide radiation having a first wavelength or range of wavelengths. The analyte sensing device 10 may also employ a plurality of radiation converting chromophores that convert and/or modify the incident radiation and provide radiation having a second wavelength or range of wavelengths. In addition, analyte sensing device 10 may employ a plurality of radiation converting chromophores that convert and/or modify the incident radiation and provide radiation having a third wavelength or range of wavelengths.

Further, one or more absorbing chromophores may be employed to absorb radiation of selected wavelength. The radiation absorbing chromophores may be implemented in conjunction with, or in lieu of, a plurality of radiation converting chromophores that convert and/or modify the incident radiation and generate radiation having a plurality of wavelengths or range of wavelengths.

In addition, it should be noted that without departing from the scope of the present invention, embodiments and modes of practice other than those explicitly discussed in detail above may be employed. For example, in the operation of analyte sensing device 10 and analyte sensing component 12, the radiation absorbing chromophore described above may, in addition to decreasing the efficiency of radiation conversion by first and/or second radiation converting chromophore 24 and/or 26, further decrease the apparent efficiency thereof by absorbing a portion of the provided radiation and thus shielding the radiation converting chromophore from the incident radiation. This secondary effect, which may also be proximity dependent, may result in an even greater change in the detected radiation conversion efficiency of first and/or second radiation converting chromophore 24 and/or 26 upon a corresponding change in analyte concentration. As such, a further enhancement of the sensitivity of analyte sensing component 12 to analyte concentration may be realized.

The technique of providing radiation to the analyte sensing device 10 may also be modified to better facilitate the detection of change in the conversion efficiency of the radiation converting element(s) of analyte sensing component 12. For example, the provided radiation may be temporally modulated in intensity and/or wavelength, and the temporal intensity and/or wavelength of the detected converted radiation may be used to determine the radiation conversion efficiency of the radiation converting element(s) of analyte sensing component 12. In one such arrangement, for example, the provided radiation may be temporally modulated in intensity according to a periodic sinusoidal profile. The detected converted radiation will also then exhibit a temporal sinusoidal intensity variation. The amplitude or phase of the sinusoidal intensity variation of the detected converted radiation relative to the provided radiation may be used to determine the conversion efficiency of the radiation converting component(s) and hence related to an analyte concentration.

Figure 10:
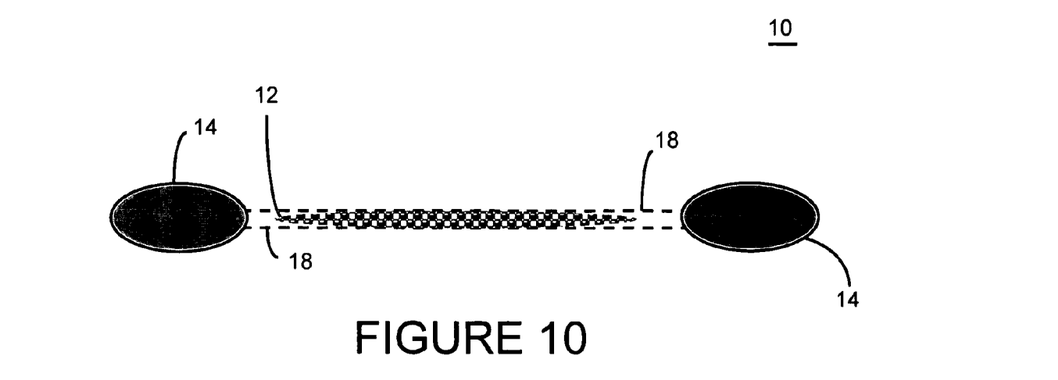
FIG. 10 is a cross-sectional view of an analyte sensing device illustrated in FIG. 1B according to another embodiment of the present invention.

Further, in an effort to enhance communication of analyte sensing device 10 with surrounding environment, the permeability of the semi-permeable portion of housing 14, namely membrane 18, may be increased (as mentioned above) and/or the surface area of membrane 18 may be increased. This may be accomplished by, for example, increasing the length/width of membrane 18 and, as such, the size of analyte sensing device 10. In addition, analyte sensing device 10 of FIGS. 1A–B may include a membrane 18 on both "sides" of analyte sensing device 10. That is, with reference to FIG. 10, membranes 18 "sandwich" analyte sensing component 12. In this way, fluid communication with the surrounding environment is increased and communication of analyte into and out of analyte sensing device 10 is enhanced.

Housing 14 and in particular semipermeable membrane may also take on a tubular or cylindrical shape. For example, a hollow dialysis fiber made of regenerated cellulose acetate may be filled with analyte sensing component 12 and sealed on the ends with, for example, cyanoacrylate or slicone adhesive. Thus, the tubular fiber forms housing 14 and allows analyte communication into and out of the housing. One or a plurality of such tubular structures may be employed to create analyte sensing device 10.

It may also be desirable to simultaneously or sequentially employ a plurality of sensor devices 10a–c having the same or different analyte sensitivities. (See, for example, FIG. 11). For example, the sensitivity of the analyte sensing component to the desired analyte may be adjusted by, for example, altering the ratio of analyte binding ligand sites to analyte-analogue molecules present in analyte sensing component 12. Such alterations may lead to sensor configurations which have optimized sensitivity over prescribed regions of analyte concentration.

For example, a first analyte sensing device may be designed to be highly sensitive at low analyte concentrations, but its signal saturates at higher analyte concentrations. A second analyte sensing device, however, may be relatively insensitive at lower analyte concentrations, but may have a much larger dynamic range before saturation. Thus, these two complementary sensor formulations may be used in conjunction to accurately cover a larger range of analyte concentration values. The two devices may be discrete or may be formulated into a single, integrated sensing device.

While the use of two (or more) radiation converting chromophores has been described in detail to address and/or compensate for variations in intervening skin optics, other, more sophisticated methods of analysis may be applied to extract the radiation converting efficiency of the first radiation converting chromophore (and hence glucose concentration). For example, it may be the case that the skin or surrounding tissues contain radiation converting chromophores which would convert radiation provided by the radiation providing unit into radiation which would "overlap" with at least a portion of the provided radiation, thereby creating interference. In this situation, it may be advantageous to employ a device and technique to discern, discriminate and/or reject that portion of the detected radiation not due to analyte sensing device 10. In this regard, a number of methods for performing such rejection are known to those skilled in the art, and it is contemplated that the use, development, and/or refinement of such methods is within the scope of the present invention. Such methods may include, for example, measurement of the conversion of radiation by skin or tissue alone, normalization of this conversion efficiency by some known quantity (for example, the intensity of radiation exiting the radiation providing means), further normalization of the detected converted radiation from both skin and first and second radiation converting chromophores together, and subsequent subtraction of the radiation converted by the skin. Other methods including multivariate regression analysis or principal component analysis may also be implemented to discern, discriminate and/or reject that portion of the detected radiation not due to analyte sensing device 10 (i.e., "isolate" contribution(s) from analyte sensing device 10).

What is claimed is:

1. An analyte sensing device for sensing a concentration of analyte in a fluid, the analyte sensing device comprising:
   a housing; and
   an analyte sensing component disposed within the housing and including:
      a first radiation converting component to convert radiation of a first wavelength to radiation having at least one different wavelength by receiving radiation of the first wavelength and, in response thereto, emitting radiation having at least one wavelength that is different from the first wavelength, wherein an efficiency of conversion by the first radiation converting component to radiation having at least one wavelength that is different from the first wavelength is dependent on the concentration of the analyte in the housing;
      a second radiation converting component to convert radiation of a second wavelength to radiation having at least one wavelength that is different from the second wavelength by receiving radiation of the second wavelength and, in response thereto, emitting radiation having at least one wavelength that is different from the second wavelength, wherein an efficiency of conversion of the radiation of the second wavelength by the second radiation converting component is independent or substantially independent of the concentration of the analyte in the housing;
      a plurality of beads or particles, wherein the second radiation converting component is embedded in or attached to at least one of the plurality of beads or particles;
      an analyte-specific binding ligand; and
      a macroporous matrix wherein (i) the analyte-specific binding ligand is attached to the macroporous matrix, and (ii) the plurality of beads or particles is embedded in the macroporous matrix.

2. The analyte sensing device of claim 1 wherein the housing includes a semi-permeable membrane.

3. The analyte sensing device of claim 2 wherein the membrane is comprised of a cellulose acetate material.

4. The analyte sensing device of claim 1 wherein the housing includes at least a permeable portion.

5. The analyte sensing device of claim 4 wherein the permeable portion of the housing is comprised of a cellulose acetate material.

6. The analyte sensing device of claim 4 wherein the housing includes a hollow dialysis fiber.

7. The analyte sensing device of claim 1 wherein the analyte-specific binding ligand is a lectin.

8. The analyte sensing device of claim 1 wherein the analyte sensing component further includes a radiation absorbing component having a proximity to the analyte-specific binding ligand that is sufficient to alter the efficiency of the conversion of the radiation of the first wavelength by the first radiation converting component.

9. The analyte sensing device of claim 1 wherein the analyte is glucose and wherein the macroporous matrix includes agarose beads and the analyte-specific binding ligand includes a lectin.

10. The analyte sensing device of claim 9 wherein the lectin is Concanavalin A.

11. The analyte sensing device of claim 1 wherein the analyte-specific binding ligand is covalently labeled with or includes a proximity to a radiation absorbing component.

12. The analyte sensing device of claim 1 wherein the analyte sensing component further comprises an analyte-analogue capable of being bound by the analyte-specific binding ligand.

13. The analyte sensing device of claim 1 wherein the analyte sensing component further includes a third radiation converting component to convert radiation of a third wavelength to at least one wavelength that is different from the third wavelength, wherein an efficiency of conversion of the radiation of the third wavelength by the third radiation converting component is dependent on the concentration of the analyte in the housing.

14. The analyte sensing device of claim 1 wherein the first and second wavelengths are the same wavelength.

15. The analyte sensing device of claim 1 wherein the device is capable of being implanted within subcutaneous tissue of an animal body.

16. The analyte sensing device of claim 1 wherein the analyte sensing component further comprises:
   an analyte-analogue;
   wherein the first radiation converting component is attached to the analyte-analogue and the analyte-specific binding ligand is capable of binding to the analyte and/or analyte-analogue; and
   a radiation absorbing component having a proximity to the analyte-specific binding ligand that is sufficient to alter the efficiency of the conversion of the radiation of the first wavelength by the first radiation converting component when the analyte analogue is bound by the analyte-specific binding ligand.

17. The analyte sensing device of claim 16 wherein the housing comprises a permeable or semi-permeable membrane which allows analyte to move into or out of the housing but does not allow analyte sensing component to move out of the housing.

18. The analyte sensing device of claim 16 wherein the efficiency of conversion of radiation at the first wavelength to radiation having the at least one different wavelength by the first radiation converting component decreases when the analyte-analogue is bound by the analyte-specific binding ligand.

19. The analyte sensing device of claim 16 wherein the analyte-analogue is a dextran.

20. The analyte sensing device of claim 16 wherein the analyte-analogue is a glycosylated or mannosylated protein.

21. The analyte sensing device of claim 18 wherein the analyte-analogue includes a polymeric chain of glucose residues.

22. The analyte sensing device of claim 16 wherein the first radiation converting component is Alexa647.

23. The analyte sensing device of claim 16 wherein the analyte-specific binding ligand is a lectin.

24. The analyte sensing device of claim 23 wherein the lectin is Concanavalin A.

25. The analyte sensing device of claim 23 wherein the lectin is *Lens culinaris* lectin.

26. The analyte sensing device of claim 16 wherein the radiation absorbing component is QSY21.

27. The analyte sensing device of claim 16 wherein the radiation absorbing component is covalently bound to the analyte-specific binding ligand.

28. The analyte sensing device of claim 16 wherein the radiation absorbing component is attached to the macroporous matrix.

29. The analyte sensing device of claim 16 further including a third radiation converting component to convert radiation of a third wavelength into radiation having at least one wavelength that is different from the third wavelength by receiving radiation of the third wavelength and, in response thereto, emitting radiation having the at least one wavelength that is different than the third wavelength.

30. The analyte sensing device of claim 1 wherein the second radiation converting component is LD800.

31. The analyte sensing device of claim 16 wherein the analyte is glucose.

32. An analyte sensing system for sensing a concentration of analyte in a fluid, the analyte sensing system comprising:
   an analyte sensing device including:
      a housing; and
      an analyte sensing component disposed within the housing and including:
         a first radiation converting component to convert radiation of a first wavelength to radiation having at least one different wavelength by receiving radiation of the first wavelength and, in response thereto, emitting radiation having at least one wavelength that is different from the first wavelength,
         wherein an efficiency of conversion by the first radiation converting component to radiation having at least one wavelength that is different from the first wavelength is dependent on the concentration of the analyte in the housing;
         a second radiation converting component to convert radiation of a second wavelength to radiation having at least one wavelength that is different from the second wavelength by receiving radiation of the second wavelength and, in response thereto, emitting radiation having at least one wavelength that is different from the second wavelength, wherein an efficiency of conversion of the radiation of the second wavelength by the second radiation converting component is independent or substantially independent of the concentration of the analyte in the housing;
         a plurality of beads or particles, wherein the second radiation converting component is embedded in or attached to at least one of the plurality of beads or particles;
         an analyte-specific binding ligand; and
         a macroporous matrix wherein (i) the analyte-specific binding ligand is attached to the the macroporous matrix, and (ii) the plurality of beads or particles is embedded in the macroporous matrix;
   a radiation providing unit to provide radiation at the first wavelength; and
   a radiation detecting unit to detect radiation having one or more wavelengths and to output data which is representative of the intensity of the radiation emitted by the first and second radiation converting components.

33. The analyte sensing system of claim 32 further including an analysis unit to determine the concentration of analyte in the housing using the data which is representative of the intensity of the radiation emitted by the first and second radiation converting components.

34. The analyte sensing system of claim 32 wherein the radiation detecting unit includes a plurality of radiation detecting devices wherein each device is capable of detecting a wavelength-specific portion of radiation.

35. The analyte sensing system of claim 32 wherein:
the first radiation converting component converts radiation of the first wavelength to radiation having a plurality of wavelengths by receiving radiation of the first wavelength and, in response thereto, emitting radiation having the plurality of wavelengths, wherein an efficiency of conversion to the radiation having the plurality of wavelengths is dependent on the concentration of the analyte in the housing; and
the radiation detecting unit includes a plurality of radiation detecting devices to detect at least one of the plurality of wavelengths.

36. The analyte sensing system of claim 32 wherein:
the first radiation converting component converts radiation of the first wavelength to radiation having a plurality of wavelengths within a first wavelength range by receiving radiation of the first wavelength and, in response thereto, emitting radiation having the plurality of wavelengths within the first wavelength range, wherein an efficiency of conversion to the radiation having the plurality of wavelengths within the first wavelength range is dependent on the concentration of the analyte in the housing; and
the radiation detecting unit includes a plurality of radiation detecting devices to detect radiation within the first wavelength range.

37. The analyte sensing system of claim 36 wherein the radiation detecting unit includes one or more photodiode detectors or a CCD array.

38. The analyte sensing system of claim 32 wherein the radiation providing unit is disposed within or adjacent to the housing.

39. The analyte sensing system of claim 32 wherein:
the analyte sensing component further includes a third radiation converting component to convert radiation of a third wavelength to at least one different wavelength by receiving the radiation of a third wavelength and, in response thereto, emitting radiation having at least one wavelength that is different from the third wavelength, wherein an efficiency of conversion is dependent on the concentration of the analyte in the housing;
the radiation detecting unit outputs data which is representative of an intensity of the radiation emitted by the first, second and third radiation converting components; and
wherein the analyte sensing system further includes an analysis unit, coupled to the radiation detecting unit, to determine the concentration of analyte in the housing using the data output by the radiation detecting unit.

40. The analyte sensing system of claim 32 wherein the analyte sensing system further includes an analysis unit, coupled to the radiation detecting unit, to determine the concentration of analyte inside the housing using the data output by the radiation detecting unit.

41. The analyte sensing system of claim 40 wherein:
the first radiation converting component converts radiation of the first wavelength to radiation having a plurality of wavelengths within a first wavelength range by receiving radiation of the first wavelength and, in response thereto, emitting radiation having the plurality of wavelengths within the first wavelength range, wherein an efficiency of conversion to the radiation having the plurality of wavelengths within the first wavelength range is dependent on the concentration of the analyte in the housing;
a second radiation converting component to convert radiation of a second wavelength to radiation having a plurality of wavelengths within a second wavelength range by receiving radiation of the second wavelength and, in response thereto, emitting radiation having the plurality of wavelengths within the second wavelength range, wherein an efficiency of conversion to the radiation having the plurality of wavelengths within the first wavelength range is independent or substantially independent of the concentration of the analyte in the housing; and
the determination of the concentration of the analyte by the analysis unit includes (1) conditioning the data output by the radiation detecting unit and (2) computing the ratio of the intensity of the radiation in a first wavelength range corresponding to radiation emitted by the first radiation converting component and a second wavelength range corresponding to radiation emitted by the second radiation converting component.

42. An analyte sensing device for sensing a concentration of analyte in a fluid, the analyte sensing device comprising:
a housing;
an analyte-analogue disposed within the housing;
a macroporous matrix disposed within the housing;
a plurality of beads or particles disposed or embedded in the macroporous matrix;
an analyte-specific binding ligand, (i) attached to the macroporous matrix, and capable of binding to analyte and/or analyte-analogue;
a first radiation converting component, attached to the analyte-analogue, to convert radiation of a first wavelength to radiation having at least one different wavelength by receiving radiation of the first wavelength and, in response thereto, emitting radiation having at least one wavelength that is different from the first wavelength, wherein an efficiency of conversion by first radiation converting component to radiation having at least one wavelength that is different from the first wavelength is dependent on the concentration of analyte in the housing;
a second radiation converting component to convert radiation of a second wavelength to radiation having at least one wavelength that is different from the second wavelength by receiving radiation of the second wavelength and, in response thereto, emitting radiation having at least one wavelength that is different from the second wavelength, wherein an efficiency of conversion of the radiation of the second wavelength by the second radiation converting component is independent or substantially independent of the concentration of the analyte in the housing, wherein the second radiation converting component is embedded in or attached to at least one of the plurality of beads or particles; and
a radiation absorbing component, disposed within the housing, having a proximity to the analyte-specific binding ligand that is sufficient to alter the efficiency of the conversion of the radiation of the first wavelength by the first radiation converting component.

43. The analyte sensing device of claim 42 wherein the housing comprises a permeable or semi-permeable membrane which allows analyte to move into or out of the housing but does not allow analyte sensing component to move out of the housing.

44. The analyte sensing device of claim 42 wherein the efficiency of conversion of radiation at the first wavelength to radiation having the at least one different wavelength by the first radiation converting component decreases when the analyte-analogue is bound by the analyte-specific binding ligand.

45. The analyte sensing device of claim 44 wherein the analyte-analogue includes a polymeric chain of glucose residues.

46. The analyte sensing device of claim 42 wherein the analyte-analogue is a dextran.

47. The analyte sensing device of claim 42 wherein the analyte-analogue is a glycosylated or mannosylated protein.

48. The analyte sensing device of claim 42 wherein the first radiation converting component is Alexa647.

49. The analyte sensing device of claim 42 wherein the analyte-specific binding ligand is a lectin.

50. The analyte sensing device of claim 49 wherein the lectin is Concanavalin A.

51. The analyte sensing device of claim 49 wherein the lectin is *Lens culinaris* lectin.

52. The analyte sensing device of claim 42 wherein the radiation absorbing component is QSY21.

53. The analyte sensing device of claim 42 wherein the radiation absorbing component is covalently bound to the analyte-specific binding ligand.

54. The analyte sensing device of claim 42 wherein the radiation absorbing component is attached to the macroporous matrix.

55. The analyte sensing device of claim 42 further including a third radiation converting component to convert radiation of a third wavelength into radiation having at least one wavelength that is different from the third wavelength by receiving radiation of the third wavelength and, in response thereto, emitting radiation having at least one wavelength that is different from the third wavelength.

56. The analyte sensing device of claim 42 wherein the second radiation converting component is LD800.

57. The analyte sensing device of claim 42 wherein the analyte is glucose.

58. The analyte sensing device of claim 42 wherein the second radiation converting component is a TransFluoSpheres.

59. The analyte sensing device of claim 42 wherein the first and second wavelengths are the same wavelength.

60. The analyte sensing device of claim 1 wherein the second radiation converting component is a TransFluoSpheres.

61. The analyte sensing system of claim 32 wherein the second radiation converting component is LD800.

62. The analyte sensing system of claim 32 wherein the second radiation converting component is a TransFluoSpheres.

63. The analyte sensing system of claim 32 wherein the first and second wavelengths are the same wavelength.

* * * * *